(12) United States Patent
Albericio Palomera et al.

(10) Patent No.: US 7,531,506 B2
(45) Date of Patent: May 12, 2009

(54) PROCESS FOR PRODUCING TRUNKAMIDE A COMPOUNDS

(75) Inventors: Fernando Albericio Palomera, Barcelona (ES); Josep Maria Caba Naudi, Barcelona (ES); Ernest Giralt Lledó, Barcelona (ES); Ignacio Manzanares, Madrid (ES); Ignacio Rodriquez, Madrid (ES)

(73) Assignee: Pharma Mar, S.A., Madrid (ES)

( * ) Notice: Subject to any disclaimer, the term of this patent is extended or adjusted under 35 U.S.C. 154(b) by 86 days.

(21) Appl. No.: 10/473,096

(22) PCT Filed: Apr. 2, 2002

(86) PCT No.: PCT/GB02/01527

§ 371 (c)(1),
(2), (4) Date: Apr. 2, 2004

(87) PCT Pub. No.: WO02/081506

PCT Pub. Date: Oct. 17, 2002

(65) Prior Publication Data

US 2005/0014684 A1 Jan. 20, 2005

(30) Foreign Application Priority Data

Apr. 2, 2001 (GB) .................. 0108234.6

(51) Int. Cl.
*A61K 38/00* (2006.01)
*A61K 38/12* (2006.01)

(52) U.S. Cl. .................. 514/9; 530/317; 530/333

(58) Field of Classification Search .................. None
See application file for complete search history.

(56) References Cited

U.S. PATENT DOCUMENTS 6,025,466 A * 2/2000 Bowden et al. ............. 530/317

FOREIGN PATENT DOCUMENTS

WO WO 97/39025 10/1997
WO WO 97/47313 12/1997

OTHER PUBLICATIONS

Bourne et al. A backbone linker for BOC-based peptide synthesis and on-resin cyclization; synthesis of stylostatin 1. J Org Chem. 1999. vol. 64, No. 9, pp. 3095-3101.*
H.J.C. Berendsen. A Glimpse of the Holy Grail? Science (1998) 282, pp. 642-643.*
Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*

D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Zips et al. New Anticancer Agents: In Vitro and In Vivo Evaluation. Review. in vivo. 2005. vol. 19, pp. 1-8.*
Voskoglou-Nomikos et al. Clinical Predictive Value of the in Vitro Cell Line, Human Xenograft, and Mouse Allograft Preclinical Cancer Models. Clinical Cancer Research. 2003. vol. 9, pp. 4227-4239.*
Sporn et al. Chemoprevention of cancer. Carcinogenesis. 2000. vol. 21, No. 3, pp. 525-530.*
Albericio, F. et al., "On the Use of PyAOP, a Phosphonium Salt Derived from HOAt, in Solid-Phase Peptide Synthesis," *Tetrahedron Letters*, 38(27):4853-4856 (1997).
Armstrong, A. et al., "A New Method for the Preparation of Tertiary Butyl Ethers and Esters," *Tetrahedron Letters*, 29(20):2483-2486 (1988).
Barlos, K. et al., "Synthesis of Prothymosin α(ProTα)—a Protein Consisting of 109 Amino Acid Residues," *Angew. Chem. Int. Ed. Engl.*, 30(5):590-593 (1991).
Berjeron, R.J. et al., "Antineoplastic and Antiherpetic Activity of Spermidine Catecholamide Iron Chelators," *Biochem and Biophysical Res. Comm.*, 121(3):848-854 (1984).
Bollhagen, R. et al., "A New Reagent for the Cleavage of Fully Protected Peptides Synthesised on 2-Chlorotrityl Chloride Resin," *J. Chem. Soc., Chem. Commun.*, 2559-2560 (1994).
Bourne, G.T. et al., "A Backbone Linker for BOC-Based Peptide Synthesis and On-Resin Cyclization: Synthesis of Stylostatin 1," *J. Org. Chem.*, 64(9):3095-3101 (1999).
Burgess, E.M. et al., "Thermal Reactions of Alkyl N-Carbomethoxysulfamate Esters," *J. Org. Chem.*, 38(1):26-31 (1973).
Burgess, G.M. et al., "The Reactions of an N-Sulfonylamine Inner Salt," *J. Am. Chem. Soc.*, 90:4744-4745 (1968).
Caba, J.M. et al., "Solid-Phase Total Synthesis of Trunkamide A," *J. Org. Chem.*, 66(23):7568-7574 (2001).
Carroll A.R. et al., "Studies of Australian Ascidians. IV Mollamide, a Cytotoxic Cyclic Heptapeptide from the Compound Ascidian *Didermnum molle*," *Aust. J. Chem.*, 47(1):61-69 (1994).
Carroll, A.R. et al., "Patellins 1-6 and Trunkamide A: Novel Cyclic Hexa-, Hepta- and Octa-peptides from Colonial Ascidians, *Lissoclinum* sp.," *Aust. J. Chem*, 49(6):659-667 (1996).
Chao, H. et al., "A Novel and Versatile Silicon-Derived Linkage Agent, 4-1-hydroxy-2-(trimethylsylil)ethyl Benzoic Acid, Compatible with the FMOC/t-Bu Strategy for Solid Phase Synthesis of C-Terminal Peptide Acids," *J. Am. Chem. Soc.*, 116(5):1746-1752 (1994).
Chiva, C. et al., "An HPLC-ESMS Study on the Solid-Phase Assembly of C-Terminal Proline Peptides," *J. Pept. Sci.*, 5:131-140 (1999).

(Continued)

*Primary Examiner*—Anish Gupta
*Assistant Examiner*—Marcela M Cordero Garcia
(74) *Attorney, Agent, or Firm*—Fish & Richardson P.C.

(57) ABSTRACT

Trunkamide A and other cycloheptapeptides can be made by solid phase synthesis of a linear precursor.

30 Claims, No Drawings

OTHER PUBLICATIONS

Galéotti, N. et al., "Formation of Oxazolines and Thiazolines in Peptides by the Mitsunobu Reaction," *Tetrahedron Letters*, 33(20):2807-2810 (1992).

Lafargue, P. et al., "(Diethylamino)Sulfur Trifluoride (Dast) as a Useful Reagent for the Preparation of 2-Oxazolines from 1,2-Amido Alcohols," *Heterocycles*, 41(5):947-958 (1995).

Lloyd-Williams, P. et al., "Chemical Approaches to the Synthesis of Peptides and Proteins," *CRC Press*, 1997. (Cover and Table of Contents only).

McKeever, B. et al., "Total Synthesis of the Prenylated Cyclopeptide Trunkamide A, a Cytotoxic Metabolite from *Lissoclinum* sp.," *Tetrahedron Letters*, 42(13):2573-2577 (2001).

Shalaby, M.A. et al., "Thiopeptide Synthesis. α-Amino Thionoacid Derivatives of Nitrobenzotriazole as Thioacylating Agents," *J. Org. Chem.*, 61(25):9045-9048 (1996).

von Halasz, S.P. et al., "Preparation of new Aminosulfur Monofluoride Imides and Aminosulfur Oxide Monofluoride Imides and the Structure of Aminosulfur Oxide Trifluorides," *Chem. Ber.*, 103:594-602 (1970).

Wifp, P. et al., "Total Synthesis and Revision of Stereochemistry of the Marine Metabolite Trunkamide A," *J. Org. Chem.*, 65(4):1037-1049 (2000).

Wipf, P. et al., "Total Synthesis of the Putative Structure of the Marine Metabolite Trunkamide A," *Tetrahedron Letters*, 40:5165-5169 (1999).

Wipf, P. et al., "Thiolysis of Oxazolines: A New, Selective Method for the Direct Conversion of Peptide Oxazolines into Thiazolines," *Tetrahedron Letters*, 36(36):6395-6398 (1995).

Yuuya et al., :Guaianolides as Immunomodulators. Synthesis and Biological Activities of Dehydrocostus Lactone, Mokko Lactone, Eremanthin and Their Derivatives, J. Nat. Prod., 1999, vol. 62, pp. 22-30.

* cited by examiner

```
                    SEQUENCE LISTING

<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: 3, 4
<223> OTHER INFORMATION: 1,1-dimethilallyl modified base
<220> FEATURE:
<221> NAME/KEY: VARIANT
<222> LOCATION: 2
<223> OTHER INFORMATION: thiazoline

<400> SEQUENCE: 1

Leu Phe Thr Ser Ile Ala Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: 3, 4
<223> OTHER INFORMATION: Tert-butyl modified base
<220> FEATURE:
<221> NAME/KEY: VARIANT
<222> LOCATION: 2
<223> OTHER INFORMATION: thiazoline
```

```
<400> SEQUENCE: 2

Leu Phe Thr Ser Ile Ala Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: oxazoline
<220> FEATURE:
<221> NAME/KEY: MOD_RES
<222> LOCATION: 3, 4
<223> OTHER INFORMATION: Tert-butyl modified base

<400> SEQUENCE: 3

Leu Phe Thr Ser Ile Ala Pro
1               5
```

PROCESS FOR PRODUCING TRUNKAMIDE A COMPOUNDS

The present invention is directed to a synthetic process for the formation of Trunkamide A and related structures.

BACKGROUND OF THE INVENTION

Trunkamide A is a cyclic heptapeptide cyclo[D-Phe-Tzn-Thr(rPr)-Ser(rPr)-Ile-Ala-Pro] isolated from the colonial ascidian *Lissoclinum* sp. Trunkamide A was first isolated by Bowden and co-workers (Carroll, A. R.; Coil, J. C.; Bourne, D. J.; McLeod, J. K.; Zabriskie, T. M.; Ireland, C. M.; Bowden, B. F. Aust. J. Chem. 1996, 49, 659-667) but the absolute configuration of the stereocentre exocyclic to the heterocyclic ring was assigned to the L-configuration. More recently Wipf and co-workers have first demonstrated that the initial assignation was erroneous (Wipf, P.; Uto, Y. Tetrahedron Lett. 1999, 40, 5165-5169) and later demonstrated that the stereocentre at C(45) has a D-configuration (Wipf, P.; Uto, Y. J. Org. Chem. 2000, 65, 1037-1049).

Thus, the structure of trunkamide A is:

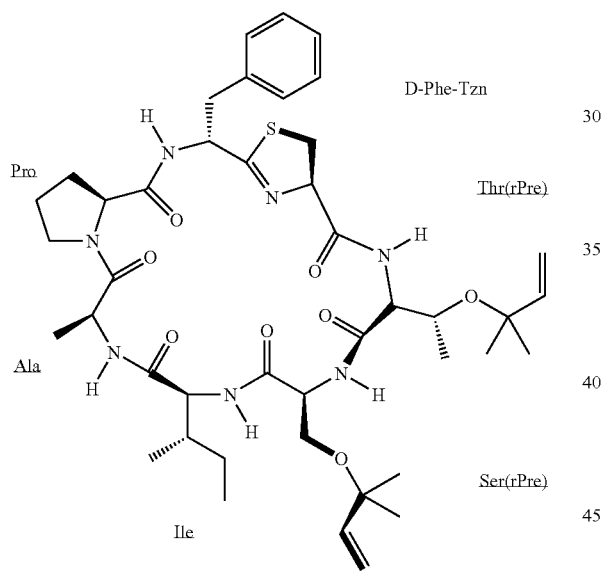

The D-Phe-Tzn is formed from two amino acids, which we refer to as amino acids one and seven of the cycloheptapeptide, where the D-Phe is amino acid seven.

Trunkamide A has promising antitumor activity and is the subject of WO 9739025.

In the article J. Org. Chem. 2000, 65, 1037-1049, Wipf and co-workers provide a synthesis of trunkamide A which involves a ring closure in solution between alanine and isoleucine to form a cycloheptapeptide having an oxazoline in place of the thiazoline ring. Trunkamide A is then obtained by further processing. The authors mention that they explored other possibilities for ring closure, such as the proline/phenylalanine amide, but they were unable to provide a viable alternative.

A further synthesis in solution by McKeever and Pattenden of trunkamide A is now also to be seen in Tetrahedron Letters 42 (2001) 2573-2577.

SUMMARY OF THE INVENTION

The present invention provides a new synthesis of trunkamide A and related compounds, along with new trunkamide A derivatives.

In particular, the invention involves the preparation of a cycloheptapeptide by a solid phase synthesis of a linear heptapeptide precursor.

The invention is especially directed at the preparation of a cycloheptapeptide containing a 5-membered heterocyclic ring as part of the backbone of an amino acid, such as thiazoline. To this end, the invention involves the preparation of a cycloheptapeptide by a solid phase synthesis of a linear heptapeptide precursor, where the linear precursor includes the ring or includes functional groups suited to form the ring. In this aspect of the invention, the process comprises solid phase synthesis of a linear peptide precursor set up for cyclisation, the precursor either being set up for heterocyclic ring formation or containing the heterocyclic ring, cyclising the linear heptapeptide and if necessary forming the heterocyclic ring.

Typically the 5-membered heterocyclic ring is of the formula: wherein X is independently O, S, or NH; each Y is independently C or CH; Z

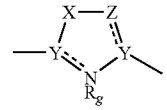

is independently CH or $CH_2$; $R_g$ is H or an organic group or is absent; and each dash line indicates a permitted second bond.

Thus products of this invention take the general form:

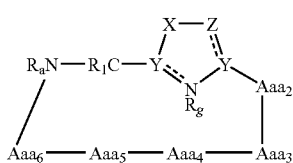

where $Aaa_2$, $Aaa_3$, $Aaa_4$, $Aaa_5$, and $Aaa_6$ are independently α-amino acid residues, $R_1$ is H or an organic group; and $R_g$, X, Y, Z and the dash line are as defined. The heterocyclic ring is formed through fusion of part of an amino acid $Aaa_1$ with an amino acid $Aaa_7$.

The synthetic process of the present invention enables the formation of compounds such as those of the following formula (III):

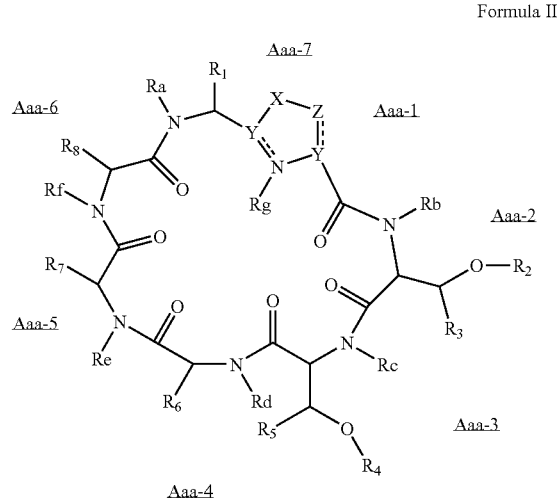

Formula III wherein Aaa$_2$, Aaa$_3$, Aaa$_4$, Aaa$_5$, and Aaa$_6$ are independently α-amino acids of L or D configuration, if applies; wherein Aaa$_1$ with Aaa$_7$ gives an amino azole five member heterocyclic ring; wherein R$_1$, R$_2$, R$_3$, R$_4$, R$_5$, R$_6$, R$_7$, R$_8$ are each independently H or an organic group selected from the group consisting of an alkyl group, an alkenyl group, an aryl group, an aralkyl group, and their substituted derivatives with an hydroxy group, a mercapto group, an amino group, a guanidino group, a halogeno group; wherein X is independently O, S, or NH; wherein R$_a$, R$_b$, R$_c$, R$_d$, R$_e$, R$_f$, and R$_g$ are each independently H or an organic group selected from the group consisting of an alkyl group and R$_g$ may be absent; wherein the pairs R$_a$-R$_1$, R$_b$-R$_3$, R$_c$-R$_5$, R$_d$-R$_6$, R$_e$-R$_7$, and R$_f$-R$_8$ can form part of the same alkyl group and therefore the corresponding amino acids are cyclic ones; wherein Y is independently C or CH; wherein each Z is independently CH or CH$_2$; and the dash line indicates a permitted second bond; with the exception of trunkamide A and the stereoisomer have the L-configuration at the C(45) stereocentre.

Pharmaceutical compositions of the compounds are provided, along with the use of the compounds in preparing such compositions and the use of the compounds in methods of treatment.

PREFERRED EMBODIMENTS OF THE INVENTION

The preferred solid phase is a super-acid labile chlorotrityl chloride resin. The solid phase synthesis preferably starts with amino acid six, then adding amino acids five, four, three, two, one and seven in that order. The numbering of the amino acids is based on that of trunkamide A. The peptide chain is preferably lengthened using a fluorenylmethyloxycarbonyl base strategy.

The process of the invention involves cyclising a linear heptapeptide and forming the heterocyclic ring. The cyclising step can be before or after the ring forming step. The ring is usually formed between functional groups from two amino acids of the cyclic heptapeptide, designated amino acids one and seven. In the present invention, the cyclising typically occurs between the COOH of amino acid six and the NH$_2$ of amino acid seven, taking the heterocyclic ring as being formed by fusion between amino acids one and seven.

In one version, the process comprises cyclising a linear heptapeptide set up for heterocyclic ring formation to give a cycloheptapeptide set up for heterocyclic ring formation, and then forming the heterocyclic ring. Such a process can include the step:

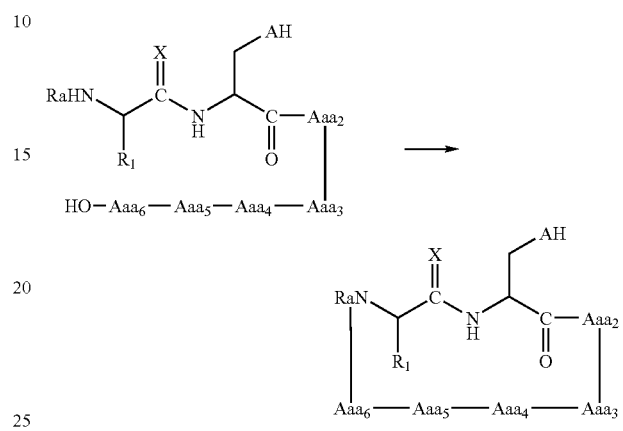

where Aaa$_2$, Aaa$_3$, Aaa$_4$, Aaa$_5$ and Aaa$_6$ represent amino acids, X is O or S, and A is O or NH, and Ra is as defined, usually H. R$_1$ is H or an organic group. The intermediate product can then be ring closed to an azoline. Where C=X is C=S, the ring is thiazoline. The C=S can be replaced by C=O to give an oxazoline. For an imidazoline, the C=S is replaced by C=O and the OH is replaced by NH$_2$. Preferably X is O or S and the closed ring is an oxazoline or thiazoline, and more preferably X is S and the closed ring is a thiazoline.

In an alternate version of the present process, the process comprises forming by solid phase synthesis a linear heptapeptide precursor including the heterocyclic ring and then cyclising the linear heptapeptide. Ordinarily the ring is formed when adding amino acid seven. Such a process can include the step:

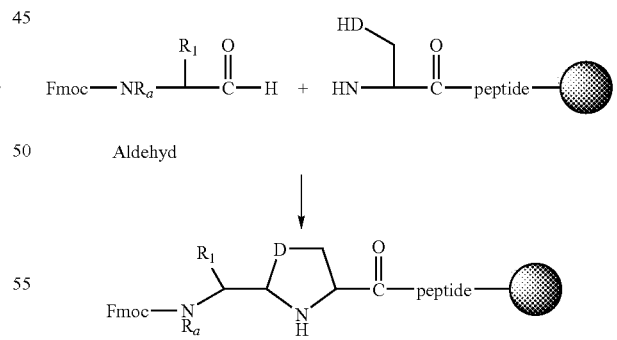

where Fmoc is a protecting group such as fluorenylmethyloxycarbonyl, peptide is Aaa$_2$, Aaa$_3$, Aaa$_4$, Aaa$_5$ and Aaa$_6$ which represent amino acids, the filled sphere is a solid phase, R$_a$ and R$_1$ are as defined, and D is S, O or NH.

In a modification of this alternate version, the saturated heterocyclic ring formed is further reacted to form an aromatic heterocyclic ring giving a thiazole, oxazole or imidazole, reflecting the identity of D.

In particular, the process of this invention can proceed in accordance with the following steps:

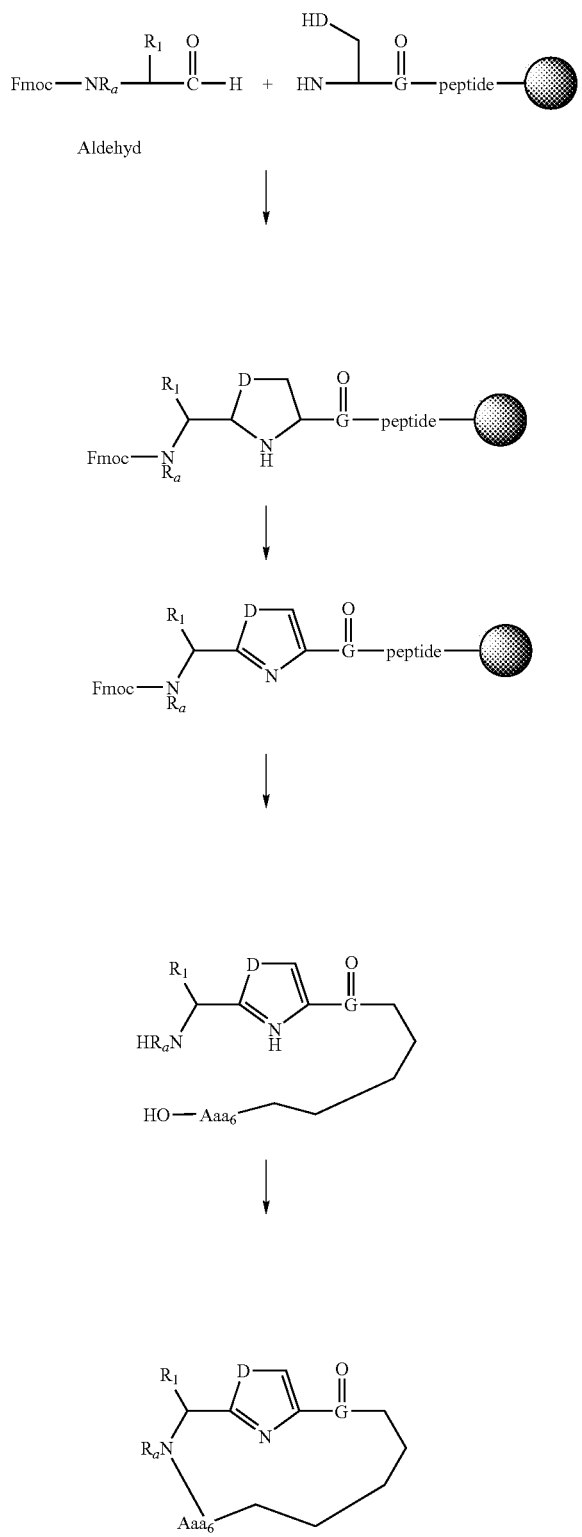

The process of the present invention is especially suited for cycloheptapeptides having reverse prenyl substituents.

The present invention is suited for the preparation of new analogues of trunkamide A, being of formula (III). A preferred group of compounds is of formula (II):

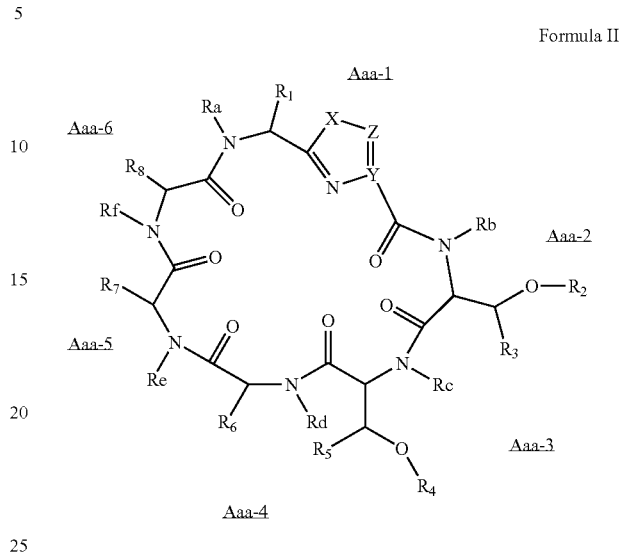

Formula II wherein $Aaa_2$, $Aaa_3$, $Aaa_4$, $Aaa_5$, and $Aaa_6$ are independently α-amino acids of L or D configuration, if applies; wherein $Aaa_1$ is independently an amino azole five member heterocyclic; wherein $R_1$, $R_2$, $R_3$, $R_4$, $R_5$, $R_6$, $R_7$, $R_8$ are each independently H or an organic group selected from the group consisting of an alkyl group, an alkenyl group, an aryl group, an aralkyl group, and their substituted derivatives with an hydroxy group, a mercapto group, an amino group, a guanidino group, a halogeno group; wherein X is independently O, S, or NH; wherein $R_a$, $R_b$, $R_c$, $R_d$, $R_e$, and $R_f$ are each independently H or an organic group selected from the group consisting of an alkyl group; wherein the pairs $R_a$-$R_1$, $R_b$-$R_3$, $R_c$-$R_5$, $R_d$-$R_6$, $R_e$-$R_7$, and $R_f$-$R_8$ can form part of the same alkyl group and therefore the corresponding amino acids are cyclic ones; wherein Y is independently C or CH; wherein Z is independently CH or $CH_2$.

As used herein, the term "organic group" means a hydrocarbon group that is classified as an aliphatic group, cyclic group, or combination of aliphatic and cyclic groups (e.g., aralkyl groups). In the context of the present invention, the term "aliphatic group" means a saturated or unsaturated linear or branched hydrocarbon. This term is used to encompass alkyl, alkenyl, and alkynyl groups, for example. The term "alkyl group" means a saturated linear or branched hydrocarbon group including, for example, methyl, ethyl, isopropyl, isobutyl, t-butyl, heptyl, decyl, octadecyl, amyl, 2-ethylhexyl, 2-methylbutyl, 5-methylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group. The term "heterocyclic group" means a closed ring hydrocarbon in which one or more of the atoms in the ring is an element other than carbon (e.g., nitrogen, oxygen, sulfur, etc.).

As is well understood in this technical area, a large degree of substitution is not only tolerated, but is often advisable. Substitution is anticipated on the compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl group or other conventional substitution. Where the term "moiety" is used to describe a chemical compound or substituent, only a unsubstituted chemical material is intended to be included. For example, the phrase "alkyl group" is intended to include not only pure open chain saturated hydrocarbon alkyl substituents, such as methyl, ethyl, propyl, isobutyl, and the like, but also alkyl substituents bearing further substituents known in the art, such as hydroxy, alkoxy, amino, carboxyl, carboxamido, halogen atoms, cyano, nitro, alkylsulfonyl, etc. Thus, "alkyl group" includes ether groups, haloalkyls, alcohols, thiols, carboxyl, amines, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, isobutyl, and the like.

When one or more of the pairs $R_a$-$R_1$, $R_b$-$R_3$, $R_c$-$R_5$, $R_d$-$R_6$, $R_e$-$R_7$, and $R_f$-$R_8$ form part of the same alkyl group and therefore the corresponding amino acids are cyclic ones, it is preferred that the amino acid is proline or a related amino acid. Such considerations apply particularly for $R_f$-$R_8$.

A preferred embodiment of the compounds represented by Formula II is trunkamide A (I), wherein Aaa-1 is D-Phe-L-Tzn ($R_a$=H, X=S, $R_1$=benzyl, Y=CH, Z=$CH_2$), Aaa-2 L-Thr(rPre) ($R_b$=H, $R_2$=1,1-dimethylallyl, $R_3$=methyl), Aaa-3 is LSer(rPre) ($R_c$, $R_5$=H , $R_4$=1,1-dimethylallyl), Aaa-4 is L-Ile ($R_d$=H, $R_6$=1-methylpropyl), Aaa-5 is L-Ala ($R_e$=H, $R_7$=methyl), and Aaa-6 is L-Pro ($R_f$=$CH_2$, $R_6$=$CH_2$—$CH_2$).

Derivatives of trunkamide A include compounds wherein $R_2$ and/or $R_4$ is an alkyl group such as methyl, t-butyl, an allyl group, or an aralkyl group such as benzyl. Further derivatives include those compounds where $R_1$ is a substituted aralkyl group, especially a para-substituted benzyl group, for example p-fluoro- or p-trifluoromethyl-benzyl. Other examples include compounds where $R_1$ is optionally substituted heteroaryl such as indole, imidazole, thiazole, or optionally substituted aryl such as phenyl.

Another compound to be made by the present process is mollamide, see Aust. J. Chem. 1994 47 61.

The compounds of the present invention have antitumour activity, and are of use in a method of treating any mammal, notably a human, affected by cancer which comprises administering to the affected individual a therapeutically effective amount of a compound of the invention, or a pharmaceutical composition thereof.

Examples of pharmaceutical compositions of this invention include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;.

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics; and l) other bioactive compounds of marine origin, notably the didemnins such as aplidine and the ecteinascidins such as ecteinascidin 743;

The preferred synthetic process of the present invention when applied illustratively to the preparation of trunkamide A is best represented in the Scheme 1:

Scheme 1

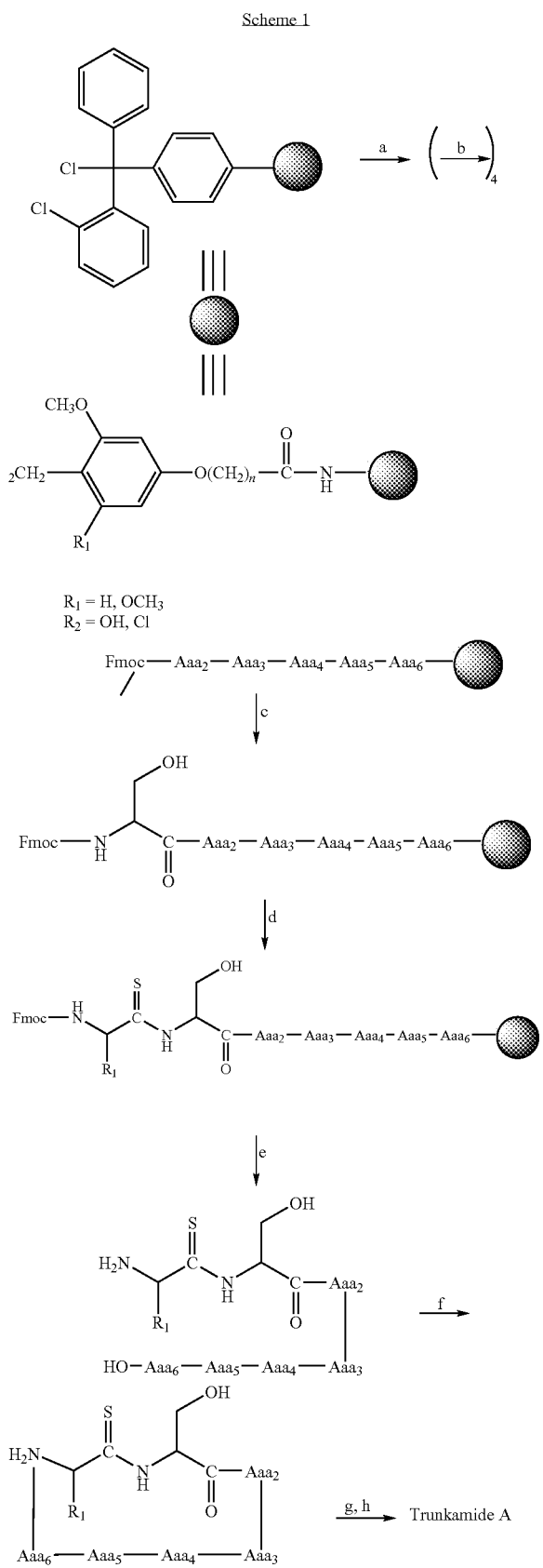

$R_1$ = H, $OCH_3$
$R_2$ = OH, Cl

As shown above in Scheme 1, the preferred process for the synthetic formation of Trunkamide A (I) and derivatives and analogues is based in a solid-phase approach and comprises the sequential steps of:

(a) incorporating a Fmoc-amino acid ($Aaa_6$) onto a solid support (e.g., polystyrene, polyethylene grafted on polystyrene, and the like) containing a super-acid labile handle or linker (e.g., chlorotrityl, polyalkoxybenzyl, and the like) forming an ester bond;

(b) elongating the peptidic chain with four amino acids ($Aaa_5$, $Aaa_4$, $Aaa_3$, $Aaa_2$) using a Fmoc/tBu strategy;

(c) incorporating Fmoc-Ser-OH with the hydroxy side-chain function unprotected;

(d) incorporating the Fmoc-Phe(S)—OH through its 6-nitrobenzotriazole derivative;

(e) cleaving the side-chain protected peptide from the solid support;

(f) cyclizing through the peptide bond;

(g) performing the thiazoline formation;

(h) removing, if applies, the side chain protecting groups different of the isoprenyl.

This process is enantio- and stereocontrolled and fast, taking advantages of the solid-phase synthetic methodology, where the molecule in construction is bounded to an insoluble support during synthetic operations, see Lloyd-Williams, P.; Albericio, F.; Giralt, E. Chemical Approaches to the Synthesis of Peptides and Proteins. CRC Press, Boca Raton (Fla.), 1997. Thus, excess of reagents and soluble by-products can be removed simply by washing the molecule-resin with suitable solvents. Large excesses of the soluble reagents can, therefore, be used in order to drive the reactions to completion in a short period of time, avoiding racemisation (if applies) and other secondary reactions. The method is also amenable for automation.

The process of this invention for trunkamide A involves a ring closure between Aaa-1 and Aaa-6, in preference to ring closure between other Aaa's.

A final step of this process for trunkamide A after peptide ring closure involves formation of the ring that is part of Aaa-1. The procedure is readily modified to give other heterocylic derivatives. Formula (II) covers thiazoline, oxazoline and imidazoline and the aromatic derivatives: thiazole, oxazole, and imidazole, while formula (III) also includes thiazolidine, oxazolidine and imidazolidine.

For Trunkamide A, the relevant reaction is between the Ser-peptide bounded to the resin and Fmoc-D-Phe(S)—Bt, giving the thia compound. For an oxa derivative, it is between the Ser-peptide bounded to the resin and and Fmoc-D-Phe-OH in the presence of a coupling reagent (for instance, DIPCDI). For the azo (an N instead of S or O), the reaction will be between a diaminopropionic acid. (Dapa)-peptide bonded to the resin and the chloroimidate of Fmoc-D-Phe-OH.

For the preparation of the other rings, the key reaction will be between the Fmoc-D-Phe-H (it is the aldehyde derivative of Fmoc-D-Phe-OH) and Cys-peptide bonded to the resin for S; ser-peptide bonded to the resin for O; and dapa-peptide bounded to the resin for N. This step gives the unsaturated heterocyclic ring and can be followed by aromatisation with $MnO_2$.

The procedure of the invention is especially suited for compounds with susceptible substituents, such as where one or both $R_2$ and $R_4$ is 1,1-dimethylallyl.

The preferred process takes advantage of the solid-phase approach, which is efficient, fast, and reliable. Second, the preparation of building blocks Fmoc-Ser(rPre)-OH and Fmoc-Thr(rPre)-OH is novel and easy to scale up. Third, the introduction of Fmoc-D-Phe(S)—OH avoids the need of a sulphuration on the peptidic chain.

In comparison with the strategy proposed by Wipf [J. Org. Chem. 2000, 65, 1037-1049], the main differences in the process of the present invention are: (i) the present process employs the solid-phase approach for the elongation of the peptidic chain; Wipf uses a solution approach. (ii) the preparation of building blocks Fmoc-Ser(rPre)-OH and Fmoc-Thr (rPre)-OH for the present process is more straightforward, involves fewer synthetic steps, and is more easily to scale up; Wipf uses the regioselective opening of an aziridine ring; (iii) Wipf introduce the Phe residue as an amino acid; the present process introduces it as an amino thioacid. Wipf have to run a dehydration of the peptide to obtain an oxazoline, then opening of the oxazoline ring with $H_2S$ (a rather nasty reaction for the formation of the thioamide peptide, the same intermediate as for the present invention), and the final dehydration with DAST. This last step is common in both approaches.

In sum, the present invention offers advantages over the process described by Wipf.

The preferred process of the present invention is illustrated in Scheme 1. As shown therein, and as discussed in greater detail in the examples which follow below, this process was conducted as follows:

Preparation of both Fmoc-Aaa2-OH and Fmoc-Aaa3-OH with the hydroxy function in form of isoprenyl, when applicable, was carried out from the corresponding, Nα-Fmoc-O-t-butyl-amino acids by the following cascade of reactions: (a) protection of the carboxyl group in form of trichloroethyl ester by reaction with the alcohol, DIPCDI, and DMAP; (ii) removal of the t-butyl groups with TFA-$H_2O$ (19:1); (iii) formation of the ether by reaction with the corresponding trichloroacetimidate, see Armstrong, A.; Brackenridge, I.; Jackson, R. F. W.; Kirk, J. M. Tetrahedron Letters 1988, 29, 20, 2483-2486.; (iv) partial reduction of the triple bond to the double by catalytic hydrogenation in the presence of Pd/C and quinoline; and (v) removal of the trichloroethyl ester with Zn and $NH_4OAc$.

Fmoc-Aaa6-OH was incorporated preferably to a chlorotrityl-polystyrene resin, see Barlos, K.; Gatos, D.; Schäfer, W. Angew. Chem. Int. Ed. Engl. 1991, 30, 590-593, in the presence of DIEA keeping the level of substitution below 0.5 mmol/g (the use of higher loadings brings the presence of terminated peptides in the final product, see Chiva, C.; Vilaseca, M.; Giralt, E.; Albericio, F. J. Pept. Sci. 1999, 5, 131-140).

Couplings of Fmoc-Aaa-OH were carried out with DIPCDI (equimolar amount respect to Fmoc-Aaa-OH) in DMF for 90 min. For Fmoc-Aaa-OH and Fmoc-Aaa$_4$-OH, 5 equiv of excess was used, while that 1.7 equiv were used for Fmoc-Aaa$_3$-OH and Fmoc-Aaa$_2$-OH, and 4 equiv for Fmoc-Ser-OH.

The Fmoc-amino thioacid was incorporated in form of the 6-nitrobenzotriazole derivative, (Shalaby, M. A.; Grote, C. W.; Rapoport, H. J. Org. Chem. 1996, 61, 9045-9048) with an excess of 3 equiv for 90 min.

Removal of the Fmoc group was carried out with piperidine-DMF (2:8, v/v) (1×1 min, 3×5 min, 1×10 min). After the coupling ninhydrin test was carried out and if it was positive the coupling was repeated in the same conditions, otherwise the process was continued. Washings between deprotection, coupling, and, again, deprotection steps were carried out with DMF (5×0.5 min) and $CH_2Cl_2$ (5×0.5 min) using each time 10 mL solvent/g resin.

Cleavage of the protected peptide was accomplished by HFIP—$CH_2Cl_2$ (1:4, 4×3 min), see Bolihagen, R.; Schmiedberger, M.; Barlos, K.; Grell, E. J. Chem. Soc., Chem. Commun. 1994, 2559-2560.

Cyclisation step was carried out with PyAOP-DIEA (2:4 equiv) in DMF for 1 h, see Albericio, F.; Cases, M.; Alsina, J.; Triolo, S. A.; Carpino, L. A.; Kates, S. A. Tetrahedron Lett. 1997, 38, 4853-4856.

Formation of the thiazoline ring was performed through the activation of the β-hydroxy group of the Ser, preferably by DAST reagent, see Halasz, S. P.; Glemser, O. Chem. Ber. 1970, 103, 594-602; (b) Lafargue, P.; Guenot, P.; Lellouche, J. P. Heterocycles 1995, 41, 947-958. and subsequent displacement by the sulfur atom, see Wipf, P.; Miller, C. P.; Venkatraman, S.; Fritch, P. C. Tetrahedron Lett. 1995, 36, 6395-6398. The use of other activating reagents, such as Burguess, see Atkins, G. M.; Burgess, E. M. J. Am. Chem. Soc. 1968, 90, 4744-4745; (b) Burguess, E. M.; Penton, H. R.; Taylor, E. A. J. Org. Chem. 1973, 38, 26-31, or Mitsunobu, see Galéotti, N.; Montagne, C.; Poncet, J.; Jouin, P. Tetrahedron Lett. 1992, 33, 2807-2810 led also to the target product, but with clearly lower yields.

Cytoxicity of trunkamide A and derivatives IC50 (molar).

| Compound | P388 | A549 | HT29 | MEL28 | DU145 |
|---|---|---|---|---|---|
| Cyclo[D-Phe-Tzn-Thr(rPr)-Ser(rPr)-Ile-Ala-Pro)(9) | 1.2E–06 | 1.2E–06 | 1.2E–06 | 1.2E–05 | 1.2E–06 |
| Cyclo[L-Phe-Tzn-Thr(rPr)-Ser(rPr)-Ile-Ala-Pro]) (10)(SEQ ID NO:1) | 1.2E–06 | 1.2E–06 | 1.2E–06 | 1.2E–06 | 1.2E–06 |
| Cyclo[L-Phe-Tzn-Thr(tBu)-Ser(tBu)-Ile-Ala-Pro]. (11)(SEQ ID NO:2) | >6.2E–06 | >6.2E–06 | >6.2E–06 | >6.2E–06 | >6.2E–06 |
| Cyclo[L-Phe-Oxa-Thr(tBu)-Ser(tBu)-Ile-Ala-Pro]. (12)(SEQ ID NO:3) | 3.1E–06 | 3.1E–06 | 3.1E–06 | >6.1E–06 | >6.1E–06 |

Methodology: after Berjeron et al, Biochem and Bioph Res. Comm., 1984, 121, 3,848854
388 = Murine lymphoma.
A549 = human lung carcinoma.
HT-29 = human colon carcinoma.
MEL-28 = human melanoma.
DU145 = human prostate carcinoma.

Methodology: after Berjeron et al, Biochem and Bioph Res. Comm., 1984, 121, 3,848854 388=Murine lymphoma. A549=lung carcinoma. . HT-29=human colon carcinoma MEL-28=human melanoma. DU145=human prostate carcinoma.

EXAMPLES OF THE INVENTION

General Procedures. Cl-TrtCl-resin, protected Fmoc-amino acid derivatives, HOBt, PYAOP were from PerSeptive Biosystems (Framingham, MA), Bachem (Bubendorf, Switzerland), Albatross (Montreal, Canada), and NovaBiochem (Läufelfingen, Switzerland). The synthesis of 1-(N-Fmoc-D-thionophenylalaninyl)-6-nitrobenzotriazole was carried out using the method described by Rapoport and co-workers. DIEA, DIPCDI, piperidine, Fmoc-Cl, NMM, isobutyl chloroformate, 4-nitro-1,2-phenylenediamine, $P_4S_{10}$, 2-methyl-3-butyne-2-ol, tricloroacetonitrile, TFA, DMAP, DCC, HFIP, DAST, Pd—C 10%, $CF_3SO_3H$, 2,2,2-trichloroethanol and quinoline were from Aldrich (Milwaukee, Wisc.). DMF, $CH_2Cl_2$, $CHCl_3$ and EtOAc were from SDS (Peypin, France). Acetonitrile (HPLC grade) and THF were from Scharlau (Barcelona, Spain). Hexane, $Et_2O$, and methanol were from Panreac (Moncada i Reixac, Barcelona). All commercial reagents and solvents were used as received with exception of DMF and $CH_2Cl_2$ which were bubbled with nitrogen to remove volatile contaminants (DMF) and stored over activated 4 Å molecular sieves (Merck, Darmstadt, Germany) (DMF) or $CaCl_2$ ($CH_2Cl_2$), and $Et_2O$ was stored over Na.

Solution reactions were performed in round bottom flasks. Organic solvent extracts were dried over anhydrous $MgSO_4$, followed by solvent removal at reduced pressures and <40° C. Solid-phase synthesis were carried out in polypropylene syringes (10/20 mL) fitted with a polyethylene porous disc. Solvents and soluble reagents were removed by suction. Removal of the Fmoc group was carried out with piperidine-DMF (2:8, v/v) (2×1 min, 2×20 min). Washings between deprotection, coupling, and, again, deprotection steps were carried out with DMF (5×1 min) and $CH_2Cl_2$ (5×1 min) using each time 10 mL solvent/g resin. Peptide synthesis transformations and washes were performed at 25° C. HPLC columns (Nucleosil $C_{18}$ reversed-phase column, 4.6×250 mm, 10 μm) were from Scharlau (Barcelona, Spain).

Analytical HPLC was carried out on a Shimadzu instrument comprising two solvent delivery pumps (model LC-6A), automatic injector (model SIL-6B), variable wavelength detector (model SPD-6A), system controller (model SCL-6B) and plotter (model C-R6A). UV detection was at 220 nm, and linear gradients of $CH_3CN$ (+0.036% TFA) into $H_2O$ (+0.045% TFA) were run at 1.0 mL/min flow rate from: (Condition A) 0:1 to 1:0 over 30 min; (Condition B) 1:1 to 10:0 over 30 min. Flash chromatography was carried out using silica gel 60 A C C 50-70 μm SDS (Peypin, France). Optical rotations were measured on a Perkin-Elmer 241 MC polarimeter. IR spectrums were measured on a Nicolet 510 FT-IR spectrometer. MALDI-TOF- and ES-MS analysis of peptide samples were performed in a PerSeptive Biosystems Voyager DE RP, using ACH or DHB matrices, and in a Micromass VG-quattro spectrometer. CI-MS analysis of amino acid derivatives were performed in a Hewlett Packard HP-5988A spectrometer. $^1$H-NMR (500 MHz, 200 MHz) and $^{13}$C-NMR (50 MHz) spectroscopy was performed on a Bruker DMX-500 (11.7 T) and Varian Gemini 200 (4.7 T). Chemical shifts (δ) are expressed in parts per million downfield from TMS. Coupling constants are expressed in Hertz.

Abbreviations used for amino acids and the designations of peptides follow the rules of the IUPAC-IUB Commission of Biochemical Nomenclature in *J. Biol. Chem.* 1972, 247, 977-983. The following additional abbreviations are used: ACH, α-cyano-4-hydroxycinnamic acid; CI, chemical ionization; Cl-TrtCl-resin, 2-chlorotrityl chloride-resin; DAST, (diethylamino)sulfur trifluoride; DCC, N,N'-dicyclohexylcarbodiimide; DHB, 2,5-dihydroxybenzoic acid; DIEA, N,N-diisopropylethylamine; DIPCDI, N,N'-diisopropylcarbodiimide; DMAP, 4-dimethylaminopyridine; DMF, N,N-dimethylformanide; ESMS, electrospray mass spectrometry; EtOAc, ethyl acetate; Fmoc, 9-fluorenylmethoxycarbonyl; Fmoc-Phe (S)-NBt, 1-(N-Fmoc-D-thionophenylalaninyl)-6-nitrobenzotriazole; HFIP, 1,1,1,3,3,3-hexafluoro-2-propanol; HPLC, high performance liquid chromatography; HOBt, 1-hydroxybenzotriazole; rPr, 1,1-dimethylallyl, reverse prenyl; MALDI-TOF, matrix assisted laser desorption ionisation-time of flight; MeOH, methanol; NMM, N-methylmorpholine; NMR, nuclear magnetic resonance; Oxa, oxazoline; PyAOP, 7-azabenzotriazol-1-yl-N-oxy-tris(pyrrolidino) phosphonium hexafluorophosphate; SPS, solid-phase synthesis; Tce, trichloroethanol; TFA, trifluoroacetic acid; THF, tetrahydrofuran; TMS, trimethylsilyl; Tzn, thiazoline; UV ultraviolet. Amino acid symbols denote the L-configuration unless stated otherwise. All solvent ratios are volume/volume unless stated otherwise.

Example 1

Fmoc-Ser-OTce (Scheme 2).

Fmoc-Ser(tBu)-OH (1 g, 2.6 mmol) was dissolved in $CH_2Cl_2$ (7 mL). DMAP (0.15 g, 1.3 mmol, 0.5 equiv) and 2,2,2-trichloroethanol (Tce) (0.3 mL, 3.1 mmol, 1.2 equiv) were first added, and then DCC (0.63 g, 3.1 mmol, 1.2 equiv) in $CH_2Cl_2$ (2.5 mL) was added under $N_2$ atmosphere at 0° C. The reaction mixture was allowed to stir for 18 h at room temperature. The organic reaction was cooled to 0° C., filtered and the filtrate was concentrate in vacuo. The resulting crude was dissolved in EtOAc (7 mL) and washed with 10% aqueous citric acid (2×10 mL), saturated aqueous $NaHCO_3$ (2×10 mL) and brine (2×10 mL), dried ($MgSO_4$), and concentrated in vacuo to give Fmoc-Ser(OtBu)-OTce (1.34 g), which was used without further purification.

Fmoc-Ser(tBu)-OTce was dissolved in TFA-$H_2O$ (19:1, 10 mL) and allowed to stir for 5 h. The reaction mixture was concentrated in vacuo and purified by flash chromatography (EtOAc-Hexane, 3:7) to give Fmoc-Ser-OTce (0.83 g, 1.8 mmol, 69% overall yield for the two steps).

Analytical HPLC ($t_R$ 12.2 min, condition B). $[\alpha]_D$-5.6° (c 0.01, $CHCl_3$, 23° C.).

IR (film) 3407, 1769, 1692, 1516, 1209, 1082 cm$^{-1}$.

CI-MS, calcd for $C_{20}H_{18}O_5NCl_3$ 457, found 475 [(M+$NH_4^+$, 100%].

HRMS (FAB) ES-MS, calcd 458.0329, found 458.0332.

$^1$H-NMR (200 MHz, $CDCl_3$) δ: 7.70-7.20 (8H, m, Ar), 6.05 (1H, d, J=8.0 Hz, NH), 4.85 (1H, d, J=12.0 Hz, $CH_2$ Tce), 4.67 (1H, d, J=12.2 Hz, $CH_2$ Tce), 4.60-4.54 (1H, m, α-CH Ser), 4.45-4.30 (2H, m, $CH_2$ Fmoc), 4.20-4.15 (1H, m, CH Fmoc), 4.10-3.85 (2H, m, β-$CH_2$ Ser), 3.50 (1H, bs, OH). $^{13}$C-NMR (50 MHz, $CDCl_3$) δ: 169.0 (CO Ser), 156.2 (CO Fmoc), 143.5 (C Ar), 141.1 (C Ar), 127.6 (CH Ar), 126.9 (CH Ar), 124.9 (CH Ar), 119.8 (CH Ar), 94.2 ($CCl_3$ Tce), 74.4 ($CH_2$ Tce), 67.2 ($CH_2$ Fmoc), 62.6 (β-$CH_2$ Ser), 55.9 (α-CH Ser), 46.9 (CH Fmoc).

Scheme 2

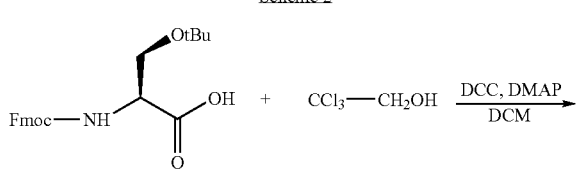

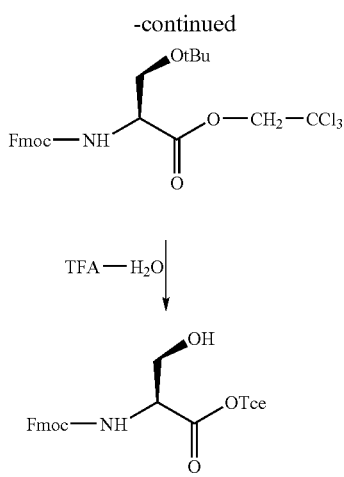

Example 2

Fmoc-Ser(rPr)—OH (Scheme 3).

Fmoc-Ser-OTce (0.83 g, 1.8 mmol) was dissolved in CH$_2$Cl$_2$-Hexane (2:1, 4 mL), and 1,1-dimethylpropinyl trichloroacetimidate (0.41 g, 1.8 mmol, 1 equiv) and CF$_3$SO$_3$H (40 μl) were added under N$_2$ atmosphere. The reaction mixture was allowed to stir for 4 days adding the same quantities of the trichloroacetimidate and CF$_3$SO$_3$H every 24 h. The reaction mixture was filtered and the filtrate was concentrated in vacuo, dissolved in EtOAc (10 mL) and washed with saturated aqueous NaHCO$_3$ (2×10 mL), H$_2$O (2×10 mL) and brine (2×10 mL). The organic solution was dried (MgSO$_4$) and concentrate in vacuo to obtain the 1,1-dimethylpropinyl ether of Fmoc-Ser-OTce (0.95 g), which was used without further purification.

The 1,1-dimethylpropinyl ether of Fmoc-Ser-OTce was dissolved in MeOH (20 mL), and Pd—C 10% (38 mg, 4% of the crude weight) and quinoline (0.44 mL, 0.45 mL per g of crude) were added under N$_2$ atmosphere. The atmosphere was changed from N$_2$ to H$_2$ and allowed to stir for 2 h. The reaction mixture was concentrated in vacuo and purified by flash chromatography (CHCl$_3$-Hexane, 8:2) to give Fmoc-Ser(rPr)-OTce (0.38 g, 0.72 mmol).

Analytical HPLC ($t_R$ 20.7 min, condition B).

$[\alpha]_D$ –26.4° (c 0.05, CHCl$_3$, 23° C.).

IR (film) 3442, 2979, 1782, 1506, 1451 cm$^{-1}$.

CI-MS, calcd for C$_{25}$H$_{26}$O$_5$NCl$_3$ 525, found 526 [(M+H)$^+$, 34%] 543 [(M+NH$_4$)$^+$, 100%].

HRMS (FAB) ES-MS, calcd 526.0955, found 526.0940.

$^1$H-NMR (200 MHz, CDCl$_3$) δ: 7.80-7.22 (8H, m, Ar), 5.82-5.65 (2H, m, CH iPr, NH), 5.20-5.10 (2H, m, CH$_2$ iPr), 4.87 (1H, d, J=10.8 Hz, CH$_2$ Tce), 4.74 (1H, d, J=10.8 Hz, CH$_2$ Tce), 4.70-4.60 (1H, m, α-CH Ser), 4.50-4.35 (2H, m, CH$_2$ Fmoc), 4.32-4.25 (1H, m, CH Fmoc), 3.90 (1H, dd, J=8.0, 2.8 Hz, β-CH$_2$ Ser), 3.60 (1H, dd, J=8.0, 2.8 Hz, β-CH$_2$ Ser), 1.26 (6H, s, 2 CH$_3$ iPr). $^{13}$C-NMR (50 MHz, CDCl$_3$) δ: 168.1 (CO Ser), 155.2 (CO Fmoc), 143.2 (C Ar), 142.6 (CH iPr), 141.1 (C Ar), 127.6 (CH Ar), 126.9 (CH Ar), 125.0 (CH Ar), 119.9 (CH Ar), 114.5 (CH$_2$ iPr), 94.0 (CC13 Tce), 75.6 (C iPr), 74.5 (CH$_2$ Tce), 67.2 (CH$_2$ Fmoc), 62.5 (β-CH$_2$ Ser), 54.4 (α-CH Ser), 47.0 (CH Fmoc), 25.6 (CH$_3$ iPr), 25.3 (CH$_3$ iPr).

Fmoc-Ser(rPr)—OTce (0.38 g, 0.72 mmol) was dissolved in THF (6 mL) and Zn dust (1.56 g, 24 mmol, 33.1 equiv) and 1 M NH$_4$OAc (1.35 mL, 1.3 mmol, 1.87 equiv) were added under N$_2$ atmosphere. The reaction mixture was allowed to stir for 14 h, filtered and concentrated in vacuo. The crude was dissolved in EtOAc (10 mL), washed with 5% aqueous KHSO$_4$ (2×10 mL) and brine (2×10 mL), dried (MgSO$_4$) and concentrated in vacuo to give Fmoc-Ser(rPr)—OH (0.28 g, 0.71 mmol, 40% overall yield for 3 steps).

Analytical HPLC ($t_R$ 11 min, condition B).

$[\alpha]_D$+11° (c 0.009, CHCl$_3$, 23° C)

IR (film) 2977, 1725, 1510, 1451, 1209 cm$^{-1}$.

CI-MS, calcd for C$_{23}$H$_2$O$_5$N 395, found: 396 [(M+H)$^+$, 18%] 413 [(M+NH$_4$)$^+$, 59%].

HRMS (FAB) ES-MS, calcd 396.1811, found 396.1814.

$^1$H-NMR (200 MHz, CDCl$_3$) δ: 7.80-7.20 (8H, m, Ar), 5.80-5.60 (2H, m, NH, CH iPr), 5.11 (1H, d, J=19.4 Hz, CH$_2$ iPr), 5.00 (1H, d, J=11.6 Hz, CH$_2$ iPr), 4.45-4.05 (4H, m, α-CH Ser, CH$_2$ Fmoc, CH Fmoc), 3.72 (1H, dd, J=9.4, 2.6 Hz, β-CH$_2$ Ser), 3.48 (1H, dd, J=9.4, 2.6 Hz, β-CH$_2$ Ser), 1.24 (6H, s, 2 CH$_3$ iPr). ).

$^{13}$C-NMR (50 MHz, CDCl$_3$) δ: 174.0 (CO Ser), 156.0 (CO Fmoc), 143.6 (C Ar), 142.7 (CH iPr), 141.1 (C Ar), 127.5 (CH Ar), 126.9 (CH Ar), 125.0 (CH Ar), 119.8 (CH Ar), 114.4 (CH$_2$ iPr), 75.7 (C iPr), 67.2 (CH$_2$ Fmoc), 62.6 (β-CH$_2$ Ser), 54.3 (α-CH Ser), 47.0 (CH Fmoc), 25.5 (2 CH$_3$ iPr).

Scheme 3

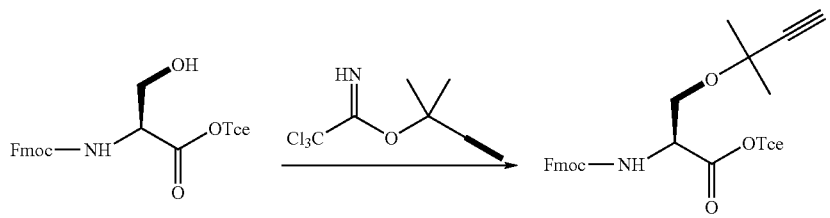

-continued

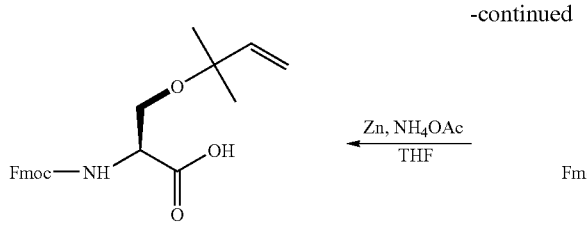

Example 3

Fmoc-Thr-OTce

According to the procedure used for the synthesis of Fmoc-Ser-OTce, Fmoc-Thr(OtBu)-OH (1 g, 2.5 mmol) provided Fmoc-Thr-OTce (0.81 g, 1.7 mmol, 68% overall yield for two steps).

Analytical HPLC ($t_R$ 14 min, condition B).

CI-MS, calcd for $C_{21}H_{20}O_5NCl_3$ 472, found 473 [(M+H)$^+$, 76%]. HRMS (FAB) ES-MS, calcd 472.0485, found 472.0486.

$^1$H-NMR (200 MHz, CDCl$_3$) δ: 7.80-7.20 (8H, m, Ar), 5.80 (1H, d, J=8.8 Hz, NH), 4.90 (1H, dd, J=12 Hz, CH$_2$ Tce), 4.70 (1H, dd, J=12 Hz, CH$_2$ Tce), 4.57-4.40 (4H, m, α-CH Thr, CH$_2$ Fmoc, β-CH Thr), 4.25-4.18 (1H, m, CH Fmoc), 2.41 (1H, bs, OH), 1.27 (3H, d, J=7 Hz, γ-CH$_3$ Thr).

$^{13}$C-NMR (50 MHz, CDCl$_3$) δ: 169.4 (CO Thr), 156.7 (CO Fmoc), 143.4 (C Ar), 141.0 (C Ar), 127.6 (CH Ar), 126.9 (CH Ar), 124.9 (CH Ar), 119.8 (CH Ar), 94.3 (Cl$_3$ Tce), 74.3 (CH$_2$ Tce), 67.5 (β-CH Thr), 67.2 (CH$_2$ Fmoc), 59.2 (α-CH Thr), 46.9 (CH Fmoc), 20.0 (γ-CH3 Thr).

Example 4

Fmoc-Thr(rPr)—OH.

According to the procedure used for the synthesis of Fmoc-Ser(OrPr)—OTce, Fmoc-Thr-OTce (0.81 g, 1.7 mmol) provided Fmoc-Thr(OrPr)—OTce (0.34 g, 0.63 mmol).

Analytical HPLC ($t_R$ 21.5 min, condition B).

$[α]_D$ 6.9° (c 0.024, CHCl$_3$, 23° C.).

IR (film) 2929, 1732, 1507, 1261, 1092 cm$^{-1}$.

ES-MS, calcd for $C_{16}H_{28}O_5NCl_3$ 539, found: m/z 540 [M+H]$^+$.

HRMS (FAB) ES-MS, calcd 540.1111, found 540.1112.

$^1$H-NMR (250 MHz, CDCl$_3$) δ: 7.80-7.30 (8H, m, Ar), 5.81-5.70 (1H, m, CH iPr), 5.66 (1H, d, J=9.5 Hz, NH), 5.2-5.12 (2H, m, CH$_2$ iPr), 4.88 (1H, dd, J=12 Hz, CH$_2$ Tce), 4.62 (1H, dd, J=12 Hz, CH$_2$ Tce), 4.45-4.40 (3H, m, α-CH Thr, CH$_2$ Fmoc), 4.35-4.20 (2H, m, CH Fmoc, β-CH Thr), 1.30-1.27 (9H, m, γ-CH$_3$ Thr, 2 CH$_3$ iPr).

$^{13}$C-NMR (50 MHz, CDCl$_3$) δ: 169.8 (CO Thr), 156.6 (CO Fmoc), 143.7 (C Ar), 143.5 (CH iPr), 141.3 (C Ar), 127.7 (CH Ar), 127.0 (CH Ar), 125.2 (CH Ar), 120.0 (CH Ar), 114.2 (CH$_2$ iPr), 94.3 (CCl$_3$ Tce), 76.0 (C iPr). 75.0 (CH$_2$ Tce), 68.0 (β-CH Thr), 67.3 (CH$_2$ Fmoc), 59.8 (α-CH Thr), 47.2 (CH Fmoc), 26.6 (CH$_3$ iPr), 26.1 (CH$_3$ iPr), 20.7 (γ-CH$_3$ Thr).

According to the procedure used for the synthesis of Fmoc-Ser(rPr)—OH, Fmoc-Thr(rPr)—OTce (0.34 g, 0.63 mmol) provided Fmoc-Thr(rPr)—OH (0.24 g, 0.6 mmol, 35% overall yield for 3 steps).

Analytical HPLC ($t_R$ 13.4 min, condition B).

ES-MS, calcd for $C_{24}H_{27}O_5N$ 409, found: m/z 410 [M+H]$^+$.

HRMS (FAB) ES-MS, calcd 410.1967, found 410.1974.

$[α]_D$ 18.3° (c 0.009, CHCl$_3$, 23° C.).

IR (film) 2979, 1726, 1506, 1451, 1211 cm$^{-1}$.

$^1$H-NMR (200 MHz, CDCl$_3$) δ: 7.80-7.20 (8H, m, Ar), 5.90-5.70 (2H, m, CH iPr, NH), 5.20 (1H, d, J=10.2 Hz, CH$_2$ iPr), 5.13 (1H, d, J=3.2 Hz, CH$_2$ iPr), 4.40-4.10 (5H, m, α-CH Thr, β-CH Thr, CH$_2$ Fmoc, CH Fmoc), 1.31 (3H, d, J=3.0 Hz, γ-CH$_3$ Thr), 1.25 (6H, s, 2 CH$_3$ iPr).

$^{13}$C-NMR (50 MHz, CDCl$_3$) δ: 173.6 (CO Thr), 156.3 (CO Fmoc), 143.5 (C Ar), 142.4 (CH iPr), 141.1 (C Ar), 127.6 (CH Ar), 126.1 (CH Ar), 125.0 (CH Ar), 119.0 (CH Ar), 114.9 (CH$_2$ iPr), 77.1 (C iPr), 67.7 (β-CH Thr), 67.2 (CH$_2$ Fmoc), 58.9 (α-CH Thr), 47.0 (CH Fmoc), 26.6 (CH$_3$ iPr), 25.6 (CH$_3$ iPr), 19.1 (γ-CH$_3$ Thr).

Example 5

H-Pro-O-TrtCl-resin.

Cl-TrtCl-resin (1 g, 1.6 mmol/g) was placed in a 20 mL polypropylene syringe fitted with a polyethylene filter disk. The resin was then washed with CH$_2$Cl$_2$ (5×1 min), and a solution of Fmoc-Pro-OH (0.27 g, 0.8 mmol, 0.5 equiv) and DIEA (0.28 mL, 1.6 mmol, 2 equiv) in CH$_2$Cl$_2$ (2.5 mL) was added, and the mixture was stirred for 1 h. The reaction was terminated by addition of MeOH (0.8 mL) and after a further stirring of 10 min. The Fmoc-Pro-O-TrtCl-resin was subjected to the following washings/treatments with CH$_2$Cl$_2$ (3×0.5 min), DMF (3×0.5 min), piperidine-DMF (1:4, 2×1, 2×20 min), DMF (5×1 min), isopropanol (2×1 min), DMF (5×1 min), MeOH (2×1 min), CH$_2$Cl$_2$ (3×1 min) and dried over vacuum.

Example 6

H-D-Phe(S)-Ser-Thr(rPr)-Ser(rPr)-Ile-Ala-Pro-O-TrtCl-resin.

Fmoc-Ala-OH (1.24 g, 4 mmol, 5 equiv), Fmoc-Ile-OH (1.4 g, 4 mmol, 5 equiv), Fmoc-Ser(rPr)—OH (0.54 g, 1.4 mmol, 1.7 equiv), Fmoc-Thr(rPr)—OH (0.56 g, 1.4 mmol, 1.7 equiv) and Fmoc-Ser-OH (1.05 g, 3.2 mmol, 4 equiv) were added sequentially to the above obtained H-Pro-O-TrtCl-resin using DIPCDI (0.62 mL, 4 mmol, 5 equiv, for Ala and Ile; 0.21 mL, 1.4 mmol, 1.7 equiv, for Ser(rPr) and Thr (rPr); 0.49 mL, 3.2 mmol, 4 equiv, for Ser) and HOBt (0.54 g, 4 mmol, 5 equiv, for Ala and Ile; 0.18 g, 1.4 mmol, 1.7 equiv, for Ser(rPr) and Thr(rPr); 0.43 g, 3.2 mmol, 4 equiv, for Ser) in DMF (7 mL, for Ala, Ile and Ser) or CH$_2$Cl$_2$ [4 mL, for Ser(rPr) and Thr(rPr)]. Finally, Fmoc-D-Phe(S)—NBt (1.32 g, 2.4 mmol, 3 equiv) in CH$_2$Cl$_2$ (7 mL) was added to the peptide resin. In all cases, after 90 min of coupling, the ninhydrin test was negative. Removal of Fmoc group and washings were carried out as described in General Procedures.

Example 7

H-D-Phe(S)-Ser-Thr(rPr)-Ser(rPr)-Ile-Ala-Pro-OH.

The peptide was cleaved from the resin by HFIP—CH$_2$Cl$_2$ (1:4, 4×3 min). The combined filtrates were evaporated to dryness under reduced pressure, to give 0.34 g of the title compound with a purity of >63% as checked by HPLC ($t_R$ 21.2 min, condition A).

ES-MS, calcd for C$_{43}$H$_{67}$N$_7$O$_{10}$S 873, found: m/z 874 [M+H]$^+$.

Example 8

Cyclo[D-Phe(S)-Ser-Thr(rPr)-Ser(rPr)-Ile-Ala-Pro].

The crude linear peptide (0.34 g, 0.39 mmol) was dissolved in CH$_2$Cl$_2$-DMF (9:1, 150 mL), and PyAOP (0.41 g, 0.78 mmol, 2 equiv) and DIEA (0.27 mL, 1.55 mmol, 4 equiv) were added. The mixture was allowed to stir for 1 h, and then the solvent was removed by evaporation under reduced pressure. The crude product was purified by flash chromatography (CHCl$_3$ MeOH, 9.8:0.2), to give the title product (100 mg, 0.12 mmol, 15% yield).

Analytical HPLC ($t_R$ 14.7 min, condition B).
ES-MS, calcd for C$_{43}$H$_{65}$N$_7$O$_9$S 855, found 856 [M+H]$^+$.
HRMS (FAB) ES-MS, calcd 856.4642, found 856.4637.
$^1$H-NMR (500 MHz, CDCl$_3$) shown in Table I.

Example 9

Trunkamide A. Cyclo[D-Phe-Tzn-Thr(rPr)-Ser(rPr)-Ile-Ala-Pro].

The cyclic peptide was dissolved in CH$_2$Cl$_2$ (1 mL), and DAST (17 µL, 0.13 mmol, 1.1 equiv) in CH$_2$Cl$_2$ (0.1 mL) was added dropwise at −20° C. under N$_2$ atmosphere. After 30 min another 1.1 equiv of DAST was added at the same conditions and allowed to stir for additional 30 min. The solvent was removed by evaporation under reduced pressure. The crude product was purified by HPLC (Vydac C$_{18}$ reversed-phase column, 15-20 µm, 250×10 mm), linear gradient from 55% to 70% of acetonitrile in water in 30 min, 3 mL/min, detection at 220 nm, to give the title product (35 mg, 0.04 mmol, 33% yield).

Analytical HPLC ($t_R$ 16.2 min, condition B).
ES-MS, calcd for C$_{43}$H$_{63}$N$_7$O$_8$S 837.5, found: m/z 838.3 [M+H]$^+$, 860.3 [M+Na]$^+$.
HRMS (FAB) ES-MS, calcd 838.4537, found 838.4556.
$^1$H-NMR (600 MHz, CDCl$_3$:d$^6$DMSO, 7:3) shown in Table II.

TABLE I

| Residue | NH | H$_\alpha$ | H$_\beta$ | Other |
| --- | --- | --- | --- | --- |
| Ala | 5.90(bs) | 4.65(qd, J=7.0Hz, 7.0Hz) | 1.23(3H, d, J=7.0Hz) | — |
| Ile | 7.19(d, J=7.0Hz) | 4.24–4.18(m) | 2.22–2.16(m) | 1.42–1.34, 1.12–1.06(2H, 2m, γCH$_2$); 0.92(3H, d, J=7.0Hz, γCH$_3$); 0.89(3H, t, J=7.5Hz, δCH$_3$) |
| Ser(OrPr) | 7.98(bs) | 4.73(ABX, J=8.0Hz, 8.0Hz, 3.5Hz) | 3.62–3.58(1H, m); 3.42–3.37(1H, m) | 5.83–5.74(1H, m, CHiPr); 5.17–5.09(2H, m, CH$_2$rPr); 1.29(6H, s, 2CH$_3$rPr) |
| Thr(OrPr) | 6.78(bs) | 4.36–4.44(m) | 4.35–4.32(m) | 5.83–5.74(1H, m, CHrPr); 5.17–5.09(2H, m, CH$_2$rPr); 1.29(6H, s, 2CH$_3$rPr); 1.11(3H, d, J 6.5Hz, γCH$_3$) |
| Ser | 8.83(bs) | 5.66–5.60(m) | 3.99(1H, dd, J= 12.5Hz, 4.0Hz); 3.62–3.58(1H, m) | — |
| D-Phe(S) | 6.56(bs) | 5.08–5.00(m) | 3.54–3.46(1H, m); 3.02(1H, dd, J=14.0Hz, 9.0Hz) | 7.29–7.23(5H, m, ar) |
| Pro | — | 4.18–4.14(m) | 3.84–3.77(1H, m, δCH$_2$); 3.54–3.46(1H, m, δCH$_2$); 2.10–2.06, 2.02–1.96, 1.92–1.76(4H, 3m, βCH$_2$, γCH$_2$) | |

TABLE II

| Residue | N—H | $H_\alpha$ | $H_\beta$ | Other |
|---|---|---|---|---|
| Ala | 7.29(d, J=5.5Hz) | 4.32(qd, J=7.4Hz, 7.4Hz) | 1.09(3H, d, J=8.4Hz) | — |
| Ile | 6.31(d, J=9.9Hz) | 4.40(dd, J=9.9, 3.3Hz) | 2.26–2.20(m) | 1.16, 1.04(2H, 2m, γ-$CH_2$); 0.88–0.82(6H, m, γ-$CH_3$, δ-$CH_3$). |
| Ser(rPr) | 7.53(d, J=8.1Hz) | 4.43(ABX, J=8.1Hz, 8.1Hz, 2.6Hz) | 3.78(1H, dd, J=10.5Hz, 2.6Hz); 3.38(1H, dd, 10.5Hz, 2.6Hz) | 5.65(1H, dd, J=17.6, 11.0Hz, CHiPr); 5.08(1H, d, J=11.0Hz, $CH_2$iPr); 5.04(1H, d, J=17.6Hz, $CH_2$iPr); 1.20(6H, s, 2$CH_3$iPr) |
| Thr(rPr) | 7.82(d, J=7.3Hz)) | 4.55(dd, J=7.3Hz, 4.8Hz) | 3.85–3.80(m) | 5.83(1H, dd, J=17.6Hz, 11.0Hz, CHiPr); 5.17(1H, d, J=17.6Hz, $CH_2$iPr); 5.13(1H, d, J=11.0Hz, $CH_2$iPr); 1.40(3H, s, $CH_3$iPr); 1.30(3H, s, $CH_3$iPr); 0.95(3H, d, J=8.1Hz, γ-$CH_3$) |
| Tzn | — | 5.00–4.91(m) | 3.67(1H, dd, J=12.3, 12.3Hz); 3.54(1H, dd, J=12.3, 12.3Hz) | — |
| D-Phe | 8.42(d, J=8.8Hz) | 5.00–4.91(m) | 3.10(1H, dd, J=16.6, 4.6Hz); 2.72(1H, dd, J=16.6, 12.5Hz) | 7.20–7.10(5H, m, Ar) |
| Pro | — | 4.26(t, J=9.4Hz) | 3.45–3.40(1H, m, δ-$CH_2$); 3.30–3.25(1H, m, δ-$CH_2$); 1.80–1.61(3H, m, β-$CH_2$, γ-$CH_2$); 1.07(1H, m, β-$CH_2$) | |

Example 10

Cyclo [L-Phe-Tzn-Thr(rPr)-Ser(rPr)-Ile-Ala-Pro] (SEQ ID NO:1).

Experimental procedures as described in Examples 1-9 were carried out with the only exception that, in Example 6, Fmoc-D-Phe(S)-NBt was replaced by Fmoc-L-Phe(S)—NBt, which was prepared from Boc-L-Phe-OH. The product was characterized.

HPLC ($t_R$ 18.8 min, Condition B),

ES-MS, calcd for $C_{43}H_{63}N_7O_8$ S, 837.5. Found: m/z 838.3 [M+H]$^+$, 860.3 [M+Na]$^+$ $^1$H-NMR (500 MHz, $CDCl_3$) shown in Table III.

TABLE III

| Residue | N—H | $H_\alpha$ | $H_\beta$ | Other |
|---|---|---|---|---|
| Ala | 7.27(d, J=7.0Hz) | 4.60–4.57(m) | 1.16(3H, d, J=6.5Hz) | — |
| Ile | 6.23(d, J=10.0Hz) | 4.65–4.63(m) | 2.43–2.37(m) | (2H, m, γ-$CH_2$); 0.95–0.90(6H, m, γ-$CH_3$, δ-$CH_3$). |
| Ser(rPr) | 7.53(d, J=7.0Hz) | 4.46–4.43(m) | 3.88(1H, dd, J=9.5Hz, 2.5Hz); 3.51–3.47(1H, m) | 5.93(1H, dd, J=17.6, 10.5Hz, CHiPr); 5.29(1H, d, J=17.5Hz, $CH_2$iPr); 5.27(1H, d, J=10.5Hz, $CH_2$iPr); 1.48(3H, s, $CH_3$iPr); 1.39(3H, s, $CH_3$iPr) |
| Thr(rPr) | 8.14(d, J=3.0Hz) | 4.60–4.57(m) | 3.98–3.94(m) | 5.27(1H, dd, J=17.5Hz, 11.0Hz, CHiPr); 5.14(1H, d, J=11.0Hz, $CH_2$iPr); 5.11(1H, d, J=17.5Hz, $CH_2$iPr); 1.25(6H, s, $CH_3$iPr); 0.95–0.90(3H, m, γ-$CH_3$) |
| Tzn | — | 4.99–4.95(m) | 3.66–3.57(2H, m) | — |
| L- | 8.43(d, J=7.0Hz) | 5.03–4.99(m) | 3.19(1H, dd, J= | 7.15–7.05(5H, m, |

TABLE III-continued

| Residue | N—H | H$_\alpha$ | H$_\beta$ | Other |
|---|---|---|---|---|
| Phe(S) | | | 14.0, 5.5Hz); 2.92(1H, dd, J=14.0, 5.5Hz) | Ar) |
| Pro | — | 4.82(t, J=7.5Hz) | 3.47–3.30(2H, m, δ-CH$_2$); 2.04–1.84(3H, m, β-CH$_2$, γ-CH$_2$); 1.70–1.54(1H, m, β-CH$_2$) | |

Example 11

Cyclo [L-Phe-Tzn-Thr (tBu)-Ser(tBu)-Ile-Ala-Pro] (SEQ ID NO:2).

Experimental procedures as described in Examples 5-9, starting with 500 mg of resin, were carried out with the following exceptions, in Example 6, Fmoc-Ser(rPr)—OH, Fmoc-Thr(rPr)—OH, and Fmoc-D-Phe(S)—NBt were replaced by Fmoc-Ser(tBu)-OH, Fmoc-Thr(tBu)-OH, and Fmoc-L-Phe(S)—NBt, respectively. The product was characterized.

HPLC (t$_R$ 18.7 min, Condition B),

MALDI-TOF-MS, calcd for C$_{41}$H$_{63}$N$_7$O$_8$S 813.5. Found: m/z 814.6 [M+H]$^+$, 836.2 [M+Na]$^+$, 852.7 [M+K]$^+$, $^1$H-NMR (500 MHz, CDCl$_3$) shown in Table IV.

Example 12

Cyclo [L-Phe-Oxa-Thr(tBu)-Ser(tBu)-Ile-Ala-Pro] (SEQ ID NO:3).

Experimental procedures as described in Examples 5-9, starting with 1 g of resin, were carried out with the following exceptions, in Example 6, Fmoc-Ser(rPr)—OH, Fmoc-Thr(rPr)—OH, and Fmoc-D-Phe(S)—NBt were replaced by Fmoc-Ser(tBu)-OH, Fmoc-Thr(tBu)-OH, and Fmoc-L-Phe(O)—OH, respectively. The product was characterized.

HPLC (t$_R$ 21.1 min, Condition A)

ES-MS, calcd for C$_{41}$H$_{63}$N$_7$O$_9$, 797.5. Found: m/z 798.1 [M+H]$^+$, $^{13}$C-NMR (200 MHz, CDCl$_3$) δ: 172.4, 170.7, 170.2, 170.1, 169.9, 168.8, 167.4, 136.3, 129.4, 128.1, 126.5, 77.2,

TABLE IV

| Residue | N—H | H$_\alpha$ | H$_\beta$ | Other |
|---|---|---|---|---|
| Ala | 7.27(d, J=5.5Hz) | 4.58–4.55(m) | 1.17(3H) | — |
| Ile | 6.21(d, J=10.0Hz) | 4.62(AX, J=10.0Hz, 3.5Hz) | 2.42–2.37(m) | 1.28–1.24(H, m, γ-CH$_2$); 1.09–1.02(H, m, γ-CH$_2$); 0.94–0.91(6H, m, γ-CH$_3$, δ-CH$_3$). |
| Ser(tBu) | 7.58(d, J=7.0Hz) | 4.47(ABX, J=7.0Hz, 3.0Hz, 3.0Hz) | 3.94(1H, dd, J=9.0Hz, 3.0Hz); 3.53(1H, dd, J=8.5Hz, 3.0Hz) | 1.15(9H, s, CH$_3$tBu) |
| Thr(tBu) | 8.19(d, J=9.0Hz) | 4.58–4.55(m) | 4.98(1H, dq, J=6.5Hz, 5.5Hz) | 1.34(9H, s, CH$_3$tBu); 0.94–0.91(3H, m, γ-CH$_3$) |
| Tzn | — | 4.99–4.96(m) | 3.63(1H, d, J=6.5Hz); 3.61(1H, d, J=7.5Hz) | — |
| L-Phe | 8.44(d, J=7.0Hz) | 5.04–4.99(m) | 3.20(1H, dd, J=14.0, 5.5Hz); 2.92(1H, dd, J=14.0, 6.0Hz) | 7.16–7.06(5H, m, Ar) |
| Pro | — | 4.83(t, J=7.5Hz) | 3.46–3.33(2H, m, δ-CH$_2$); 2.56–2.52, 2.00–1.94, 1.91–1.82, 1.65–1.56(4H, 4m, β-CH$_2$, γ-CH$_2$) | |

75.8, 73.9, 70.7, 67.8, 65.9, 61.1, 59.6, 57.5, 56.2, 55.9, 49.1, 47.7, 47.2, 37.8, 36.4, 29.7, 28.2, 27.3, 25.4, 25.1, 23.6, 18.8, 18.3, 16.0, 12.0

$^1$H-NMR (500 MHz, CDCl$_3$) shown in Table V.

TABLE V

| Residue | N—H | H$_\alpha$ | H$_\beta$ | Other |
|---|---|---|---|---|
| Ala | 7.26(d, J=5.5Hz) | 4.60–4.52(m) | 1.12(3H) | — |
| Ile | 6.19(d, J=9.5Hz) | 4.63–4.62(m) | 2.40–2.34(m) | 1.24–1.18(1H, m, γ-CH$_2$); 1.08–1.00(1H, m, γ-CH$_2$); 0.91–0.88(6H, m, γ-CH$_3$, δ-CH$_3$). |
| Ser(tBu) | 7.48(d, J=7.0Hz) | 4.46(ABX, J=6.0Hz, 3.0Hz, 3.0Hz) | 3.92(1H, dd, J=9.5Hz, 3.0Hz); 3.49(1H, dd, J=9.0Hz, 3.0Hz) | 1.13(9H, s, CH$_3$tBu) |
| Thr(tBu) | 8.08(d, J=6.5Hz) | 4.43(AX, J=7.0Hz, 6.5Hz | 4.03(1H, dq, J=6.5Hz, 6.5Hz, 5.0Hz) | 1.30(9H, s, CH$_3$tBu); 0.75(3H, d, J=6.5Hz, γ-CH$_3$) |
| Oxa | — | 4.69–4.64(m) | 4.60–4.52(2H, m) | — |
| L-Phe | 8.18(d, J=7.0Hz) | 4.91(ABX, J=7.0Hz, 3.0Hz, 3.0Hz) | 3.14(1H, dd, J=14.0Hz, J=5.0Hz); 2.92(1H, dd, J=14.0Hz, J=5.0Hz) | 7.14–6.90(5H, m, Ar) |
| Pro | — | 4.85(t, J=7.5Hz) | 3.44–3.34(2H, m, δ-CH$_2$); 2.57–2.50, 1.98–1.88, 1.65–1.56(4H, 3m, β-CH$_2$, γ-CH$_2$) | |

The complete disclosure of each documents cited herein is incorporated by reference.

---

The invention claimed is:

1. A process for preparing a cycloheptapeptide containing a 5-membered heterocyclic ring as part of the backbone of the cyclic peptide, the cycloheptapeptide being of formula (III):

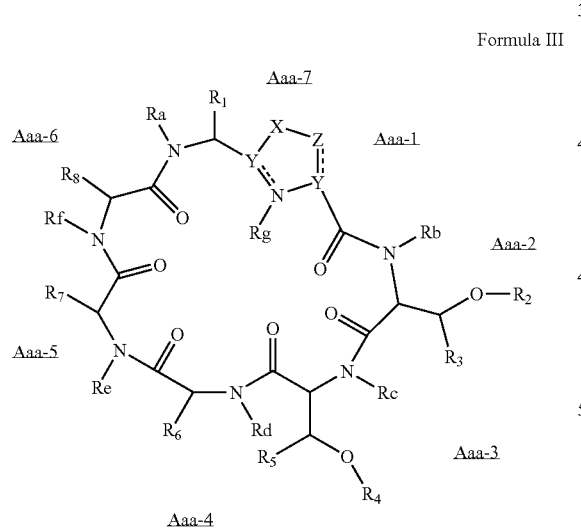

Formula III wherein $Aaa_2$, $Aaa_3$, $Aaa_4$, $Aaa_5$, and $Aaa_6$ are independently α-amino acids of L or D configuration, if applies; wherein $Aaa_1$ is independently an amino azole five member heterocyclic; wherein X is O or S;

wherein Y is independently C or CH;

Z is CH or $CH_2$;

each of the dash lines indicates a permitted second bond, with the proviso that if the second bond exists between Y and the nitrogen atom bearing $R_g$, then $R_g$ is absent;

$R_1$ is a benzyl group;

$R_2$ is selected from the group consisting of an alkyl group, an alkenyl group, and an aralkyl group and their substituted derivatives with an hydroxy group, a mercapto group, an amino group, a guanidino group, a halogeno group;

$R_4$ is selected from the group consisting of an alkyl group, an alkenyl group, an aryl group, and aralkyl group and their substituted derivatives with an hydroxy group, a mercapto group, an amino group, a guanidino group, a halogeno group;

$R_3$ and $R_5$ are each independently selected from the group consisting of H or an alkyl group and its substituted derivatives with an hydroxy group, a mercapto group, an amino group, a guanidino group, a halogeno group;

$R_6$ is 1-methylpropyl;

$R_7$ is methyl;

$R_8$ and $R_f$ form a —$CH_2CH_2CH_2$— group;

and each of $R_a$, $R_b$, $R_c$, $R_d$, $R_e$, and $R_g$ is H;

which process comprises synthezising by solid phase synthesis a linear heptapeptide precursor, the precursor either contains a heterocyclic ring or is able to form a heterocyclic ring;

cyclising the linear heptapeptide and if necessary forming the heterocyclic ring.

2. A process according to claim 1, where the solid phase is a super-acid labile chlorotrityl chloride resin.

3. A process according to claim 1, where the peptide chain is lengthened using a fluorenylmethyloxycarbonyl base strategy.

4. A process according to claim 1, which comprises cyclising a linear heptapeptide set up for heterocyclic ring formation to give a cycloheptapeptide set up for heterocyclic ring formation, and then forming the heterocyclic ring.

5. A process according to claim 4, which includes the step:

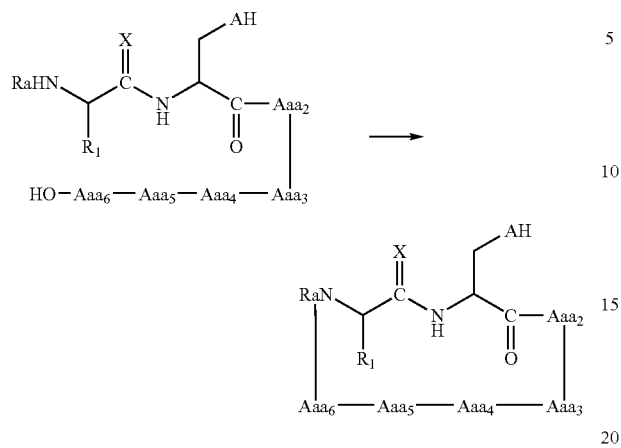

where Aaa$_2$, Aaa$_3$, Aaa$_4$, Aaa$_5$ and Aaa$_6$ represent amino acids, X is O or S, and A is O.

6. A process according to claim 5, where X is O or S and the closed ring is an oxazoline or thiazoline.

7. A process according to claim 6, wherein X is S and the closed ring is a thiazoline.

8. A process according to claim 1, which comprises forming a linear heptapeptide precursor including the heterocyclic ring and then cyclising the linear heptapeptide.

9. A process according to claim 8, which includes the step:

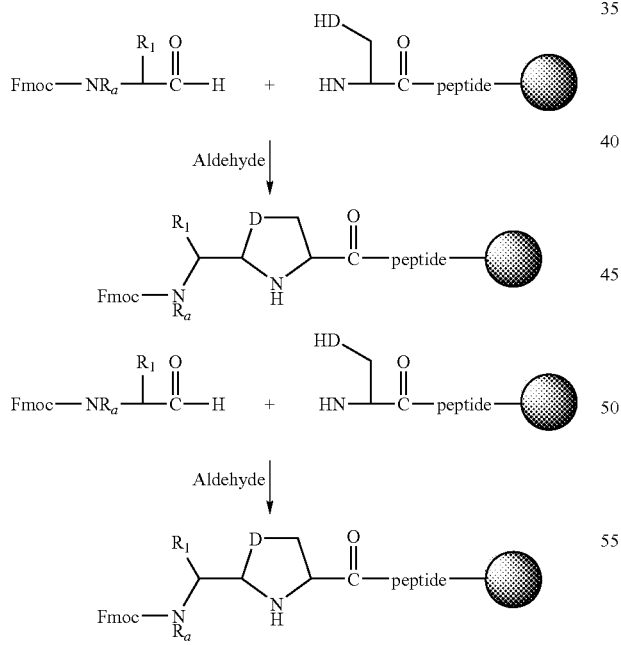

where Fmoc is fluorenylmethyloxycarbonyl, peptide is Aaa$_2$, Aaa$_3$, Aaa$_4$, Aaa$_5$ and Aaa$_6$ which represent amino acids, the filled sphere is a solid phase, and D is S, O.

10. A process according to claim 8, wherein the heterocyclic ring formed by the cyclisation of the linear heptapeptide is further reacted to form an aromatic heterocyclic ring.

11. A compound of the following formula (III):

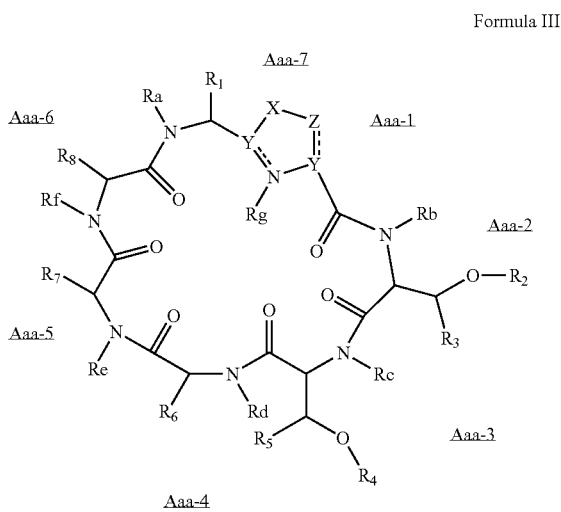

Formula III wherein Aaa$_2$, Aaa$_3$, Aaa$_4$, Aaa$_5$, and Aaa$_6$ are independently α-amino acids of L or D configuration, if applies; wherein Aaa$_1$ is independently an amino azole five member heterocyclic; wherein X is O or S;

wherein Y is independently C or CH;

Z is CH or CH$_2$;

each of the dash lines indicates a permitted second bond, with the proviso that if the second bond exists between Y and the nitrogen atom bearing R$_g$, then R$_g$ is absent;

R$_1$ is a benzyl;

R$_2$ is selected from the group consisting of an alkyl group, an alkenyl group, and an aralkyl group and their substituted derivatives with an hydroxy group, a mercapto group, an amino group, a guanidino group, a halogeno group, provided that R$_2$ is not a 1,1-dimethylallyl group;

R$_4$ is selected from the group consisting of an alkyl group, an alkenyl group, an aryl group, and aralkyl group and their substituted derivatives with an hydroxy group, a mercapto group, an amino group, a guanidino group, a halogeno group;

R$_3$ and R$_5$ are each independently selected from the group consisting of H or an alkyl group and its substituted derivatives with an hydroxy group, a mercapto group, an amino group, a guanidino group, a halogeno group;

R$_6$ is 1-methylpropyl;

R$_7$ is methyl;

R$_8$ and R$_f$ form a —CH$_2$CH$_2$CH$_2$— group;

and each of R$_a$, R$_b$, R$_c$, R$_d$, R$_e$, and R$_g$ is H;

or a pharmaceutically acceptable salt thereof.

12. The compound of claim 11, wherein

R$_2$ is a group selected from the group consisting of an alkyl group and an alkenyl group;

R$_4$ is a group selected from the group consisting of an alkyl group and an alkenyl group and an aralkyl group;

R$_5$ is H;

R$_3$ is an alkyl group;

Z is CH$_2$; and the dash line indicates a permitted second bond, with the proviso that if the second bond exists between Y and N atoms then R$_g$ is absent.

13. A pharmaceutical composition comprising a compound of the following formula (III):

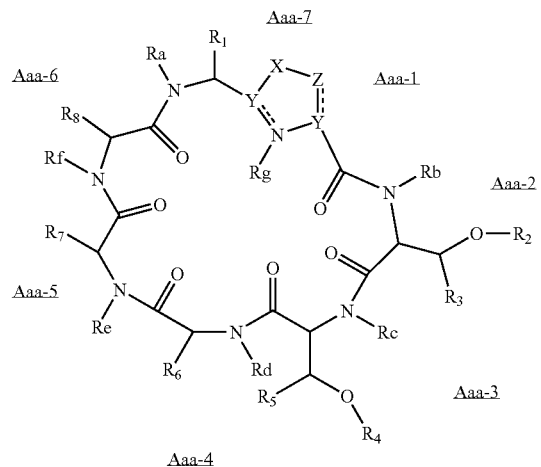

Formula III wherein $Aaa_2$, $Aaa_3$, $Aaa_4$, $Aaa_5$, and $Aaa_6$ are independently α-amino acids of L or D configuration, if applies; wherein $Aaa_1$ is independently an amino azole five member heterocyclic; wherein X is O or S;

wherein Y is independently C or CH;

Z is CH or $CH_2$; and each of the dash lines indicates a permitted second bond, with the proviso that if the second bond exists between Y and the nitrogen atom bearing $R_g$, then $R_g$ is absent;

$R_1$ is a benzyl;

$R_2$ is selected from the group consisting of an alkyl group, an alkenyl group, and an aralkyl group and their substituted derivatives with an hydroxy group, a mercapto group, an amino group, a guanidino group, a halogeno group, provided that $R_2$ is not a 1,1-dimethylallyl group;

$R_4$ is selected from the group consisting of an alkyl group, an alkenyl group, an aryl group, and aralkyl group and their substituted derivatives with an hydroxy group, a mercapto group, an amino group, a guanidino group, a halogeno group;

$R_3$ and $R_5$ are each independently selected from the group consisting of H or an alkyl group and its substituted derivatives with an hydroxy group, a mercapto group, an amino group, a guanidino group, a halogeno group;

$R_6$ is 1-methylpropyl;

$R_7$ is methyl;

$R_8$ and $R_f$ form a $—CH_2CH_2CH_2—$ group;

and each of $R_a$, $R_b$, $R_c$, $R_d$, $R_e$, and $R_g$ is H; and a pharmaceutically acceptable carrier.

14. A method of treating lung cancer, colon cancer, prostate cancer, melanoma and lymphoma which comprises administering a compound of the following formula (III):

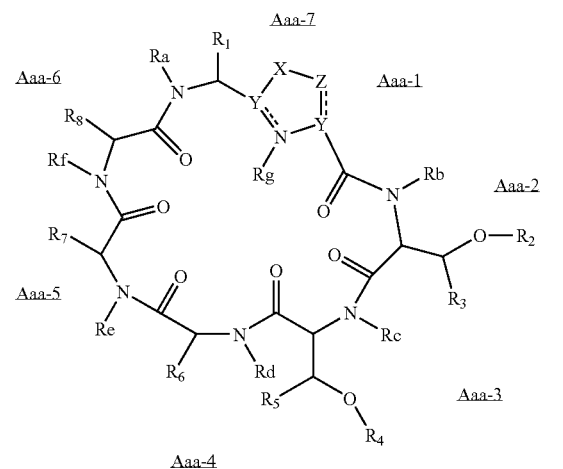

Formula III wherein $Aaa_2$, $Aaa_3$, $Aaa_4$, $Aaa_5$, and $Aaa_6$ are independently α-amino acids of L or D configuration, if applies; wherein $Aaa_1$ is independently an amino azole five member heterocyclic; wherein X is O or S;

wherein Y is independently C or CH;

Z is CH or $CH_2$;

each of the dash lines indicates a permitted second bond, with the proviso that if the second bond exists between Y and the nitrogen atom bearing $R_g$, then $R_g$ is absent;

$R_1$ is a benzyl;

$R_2$ is selected from the group consisting of an alkyl group, an alkenyl group, and an aralkyl group and their substituted derivatives with an hydroxy group, a mercapto group, an amino group, a guanidino group, a halogeno group, provided that $R_2$ is not a 1,1-dimethylallyl group;

$R_4$ is selected from the group consisting of an alkyl group, an alkenyl group, an aryl group, and aralkyl group and their substituted derivatives with an hydroxy group, a mercapto group, an amino group, a guanidino group, a halogeno group;

$R_3$ and $R_5$ are each independently selected from the group consisting of H or an alkyl group and its substituted derivatives with an hydroxy group, a mercapto group, an amino group, a guanidino group, a halogeno group;

$R_6$ is 1-methylpropyl;

$R_7$ is methyl;

$R_8$ and $R_f$ form a $—CH_2CH_2CH_2—$ group;

and each of $R_a$, $R_b$, $R_c$, $R_d$, $R_e$, and $R_g$ is H.

15. The pharmaceutical composition of claim 13, wherein $R_2$ is a group selected from the group consisting of an alkyl group and an alkenyl group;

$R_4$ is a group selected from the group consisting of an alkyl group and an alkenyl group and an aralkyl group;

$R_5$ is H;

$R_3$ is an alkyl group;

Z is $CH_2$; and the dash line indicates a permitted second bond, with the proviso that if the second bond exists between Y and N atoms then $R_g$ is absent.

16. The method of claim 14, wherein $R_2$ is a group selected from the group consisting of an alkyl group and an alkenyl group;

$R_4$ is a group selected from the group consisting of an alkyl group and an alkenyl group and an aralkyl group;

$R_5$ is H;

$R_3$ is an alkyl group;

Z is $CH_2$; and the dash line indicates a permitted second bond, with the proviso that if the second bond exists between Y and N atoms then $R_g$ is absent.

17. A method of treating lung cancer, colon cancer, prostate cancer, melanoma and lymphoma which comprises administering a composition according to claim 13.

18. A method of treating lung cancer, colon cancer, prostate cancer, melanoma and lymphoma which comprises administering a composition according to claim 15.

19. The compound of claim 11 or 12, wherein X is S and Z is —$CH_2$.

20. The pharmaceutical composition of claim 13 or 15, wherein X is S and Z is —$CH_2$.

21. The method of claim 14 or 16, wherein X is S and Z is —$CH_2$.

22. A method of treating lung cancer, colon cancer, prostate cancer, melanoma and lymphoma which comprises administering a composition according to claim 20.

23. The compound of claim 11, wherein the compound is Cyclo[L-Phe-Tzn-Thr(tBu)-Ser(tBu)-Ile-Ala-Pro] (SEQ ID NO:2).

24. The compound of claim 11, wherein the compound is Cyclo[L-Phe-Oxa-Thr(tBu)-Ser(tBu)-Ile-Ala-Pro] (SEQ ID NO:3).

25. The compound of claim 11, wherein $R_2$ is selected from the group consisting of an alkyl group, an allyl group, and an aralkyl group.

26. The compound of claim 11, wherein $R_2$ is selected from the group consisting of a methyl group, a tert-butyl group, an allyl group, and a benzyl group.

27. The compound of claim 11, wherein $R_2$ is a tert-butyl group.

28. The compound of claim 11, wherein $R_4$ is selected from the group consisting of an alkyl group, an alkenyl group, and an aralkyl group.

29. The compound of claim 11, wherein $R_4$ is selected from the group consisting of a methyl group, a tert-butyl group, an allyl group, a 1,1-dimethylallyl group and a benzyl group.

30. The compound of claim 11, wherein:

$R_2$ is selected from the group consisting of a methyl group, a tert-butyl group, an allyl group, and a benzyl group; and $R_4$ is selected from the group consisting of a methyl group, a tert-butyl group, an allyl group, a 1,1-dimethylallyl group, and a benzyl group.

\* \* \* \* \*